United States Patent [19]

Zonneveld et al.

[11] Patent Number: 4,535,245

[45] Date of Patent: Aug. 13, 1985

[54] WAVELENGTH-SENSITIVE RADIOGRAPHY APPARATUS

[75] Inventors: Frans W. Zonneveld; Cornelis Kramer, both of Eindhoven, Netherlands

[73] Assignee: U.S. Philips Corporation, New York, N.Y.

[21] Appl. No.: 602,625

[22] Filed: Apr. 23, 1984

Related U.S. Application Data

[63] Continuation of Ser. No. 311,563, Oct. 15, 1981, abandoned.

[30] Foreign Application Priority Data

Nov. 13, 1980 [NL]   Netherlands ..................... 8006216

[51] Int. Cl.³ .............................................. G01T 1/185
[52] U.S. Cl. ...................................... 250/385; 378/5; 250/374
[58] Field of Search ........................... 378/19, 116, 5; 250/385, 374; 313/93

[56] References Cited

U.S. PATENT DOCUMENTS

| | | | |
|---|---|---|---|
| 2,657,315 | 10/1953 | Goldstein | 313/93 |
| 3,974,386 | 8/1976 | Mistretta et al. | 378/99 |
| 4,029,963 | 6/1977 | Alvarez et al. | 378/5 |
| 4,247,774 | 1/1981 | Brooks | 378/5 |
| 4,253,024 | 2/1981 | Peschmann | 250/385 |
| 4,323,784 | 4/1982 | Conrad | 250/361 R |
| 4,376,893 | 3/1983 | Whetten | 250/385 |

OTHER PUBLICATIONS

Fenster, Aaron, "Split Xenon Detector for Tomochemistry in Computed Tomography," *J. of Computer Assisted Tomography*, vol. 2, pp. 243-252, (Jul. 1978).

*Primary Examiner*—Alfred E. Smith
*Assistant Examiner*—Carolyn E. Fields
*Attorney, Agent, or Firm*—Marc D. Schechter

[57] ABSTRACT

A radiography apparatus comprises a radiation source which is arranged to supply radiation spectra of different energies. The apparatus also comprises a detector which can be adjusted for the radiation spectra so that a strong wavelength discrimination occurs in the measurement signals. In a detector comprising an ionization chamber, there is arranged an auxiliary electrode which can be adjusted in phase with the radiation source so that soft radiation of a soft source spectrum or hard radiation of a hard source spectrum is comparatively favored with respect to its contribution to the measurement signal.

5 Claims, 10 Drawing Figures

WAVELENGTH-SENSITIVE RADIOGRAPHY APPARATUS

This is a continuation, of application Ser. No. 311,563, filed Oct. 15, 1981, now abandoned.

BACKGROUND OF THE INVENTION

The invention relates to radiography apparatus. The apparatus comprises a radiation source with an adjustment mechanism for generating radiation having at least two different energy spectra. It also comprises a radiation detector having an ionization chamber with a high voltage electrode, a signal electrode and an entrance window.

A radiography apparatus of this kind is known from U.S. Pat. No. 3,974,386. For many applications a clear distinction between the images formed by means of radiation having different energy spectra is very desirable. If the different energy spectra are obtained by the application of different high voltages to an X-ray tube as described in that Patent, the photons energy in the respective spectra overlap substantially. If an attempt is made to limit the overlap by more thorough filtering, either (i) the primary radiation intensity generated by the source would have to be made very high, which would reduce the life of the source or would necessitate the use of an expensive and heavy source, or (ii) one of the signals would become so weak that only very noisy images would be formed.

SUMMARY OF THE INVENTION

It is an object of the invention to provide a radiography apparatus in which measurement signals can be obtained which have improved separation without substantially increasing the loading on the source. To achieve this, a radiography apparatus according to the invention includes an auxiliary electrode in the detector. The auxiliary electrode enables, in conjunction with means connected thereto, a measurement to be made which is dependent on the wavelength of the radiation to be measured.

Because the detector sensitivity in a radiography apparatus according to the invention can be adapted to a preferred energy, clearly separated measurement signals can be obtained for different spectra even with customary X-ray source loading. Notably, a better distinction can be made between soft radiation from a first, soft wavelength spectrum and hard radiation from a second, hard wavelength spectrum of an X-ray tube.

In a preferred embodiment, the auxiliary electrode is arranged near the entrance window of the detector. The potential of the auxiliary electrode is set to approximately the potential of the high-voltage electrode for detecting the soft wavelength spectrum of the X-ray tube. In this case electrons released by ionization in the ionization chamber near the entrance window, are driven only to the signal electrode, and hence they contribute to the measurement signal. For detecting the hard wavelength spectrum, the potential of the auxiliary electrode is set substantially equal to that of the signal electrode. In this case electrons released in the ionization chamber near the entrance window, are driven onto the auxiliary electrode, so that they do not contribute to the measurement signal. Because mainly soft radiation gives rise to ionization near the entrance window, therefore the detection of soft radiation is favored when the auxiliary electrode is at the lower potential, while the soft radiation is unfavored and hence the hard radiation is comparatively favored when the auxiliary electrode is at the higher potential of the signal electrode.

For the spectral adjustment mechanism for the radiation source, one can advantageously use an X-ray generator which is marketed under the name Optimus 500 (trademark), and which features fast switching between, for example, two distinct high voltages.

Particularly for detectors used in the so-called X-ray scanners, it is advantageous to arrange the auxiliary electrode on the inner side of a radiation entrance window of each of the detector cells. If the entrance window is made of an electrically conductive material, it should be insulated electrically from the auxiliary electrode.

In a further preferred embodiment, the signal electrode is divided into two sections disposed along the longitudinal direction. The longitudinal direction is to be understood to mean herein the direction which coincides with the propagation direction of the radiation to be measured. By varying the distance between the signal electrode and the part thereof which serves as an auxiliary electrode in this configuration, a compromise can be found between better energy separation, with some loss of sensitivity, or less energy separation with a higher sensitivity.

A corresponding separation can also be used for the high voltage electrodes. This embodiment offers the advantage that the supply of the potential to the relevant electrodes is simpler, because all portions which act as auxiliary electrodes can then also be mutually short-circuited.

A further advantage of this embodiment is that difference signals can be measured directly by a suitable choice of the potentials to be supplied.

DESCRIPTION OF THE PREFERRED EMBODIMENTS

Figure 1:
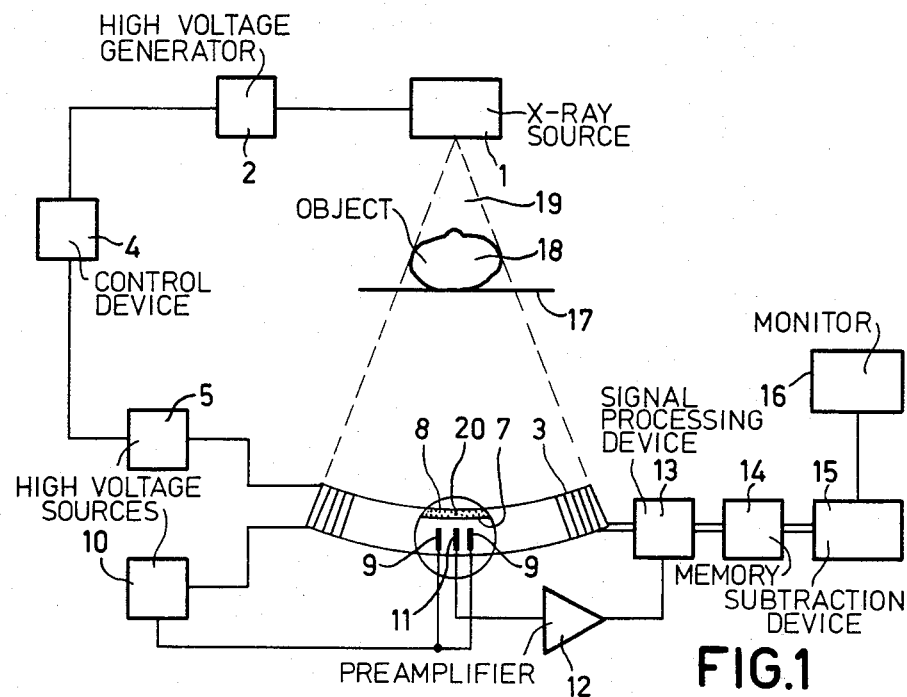
FIG. 1 is a schematic representation of a radiography apparatus according to the invention in the form of an X-ray scanner.

An X-ray scanner as shown in FIG. 1 comprises an X-ray source 1, a high voltage generator 2 for powering the X-ray source, and an array of detectors 3. Via a control device 4 and a switchable high voltage source 5, the generator 2 is connected to an auxiliary electrode 7 which is in this case arranged on an entrance window 8 of the detector. High-voltage electrodes 9 of the detector are connected to a fixed high-voltage source 10. Signal electrodes 11 are connected to a signal processing device 13 via preamplifiers 12. A memory 14, a subtraction device 15 and a monitor 16 are connected to the signal processing device 13.

An object 18, arranged on a support 17, is irradiated by an X-ray beam 19, and the local absorption of the object is measured in known manner by means of the detector. A sufficient amount of measurement data in the form of absorption values are obtained (for the reconstruction of an absorption image of an irradiated slice of the object) by rotation, in this case of the source and the detector array together about the object.

The X-ray source, in this case an X-ray tube, is adapted to generate X-rays in several, different photo-energy spectra. For the sake of simplicity, two different energy spectra are assumed herein.

A first spectrum, which is again referred to hereinafter as the soft spectrum, is emitted by the X-ray tube at a high voltage of, for example, 80 kV. A second spectrum, which is to be referred to as a hard spectrum, is emitted by the X-ray tube at, for example, 140 kV. As is known, these two spectra overlap one another to a large extent. The use of filters to remove the softer spectrum from the harder spectrum cannot eliminate the overlap, and moreover necessitates an extremely high X-ray tube loading. For switching between two spectra, therefore, the use of a filter is not suitable. For high switching rates, the mechanical movement also becomes objectionable.

Therefore, a solution is implemented in which an image is formed for each of these two spectra. Each image provides the relevant information for that radiation. Therefore, an attempt must be made to minimize the disturbing effect of hard radiation in the soft spectrum image and, conversely, to minimize the disturbing effect of soft radiation in the hard spectrum image. Usually it is also desirable that both images can be formed preferably simultaneously, but in any case in rapid succession within fractions of a second.

Figure 2A:
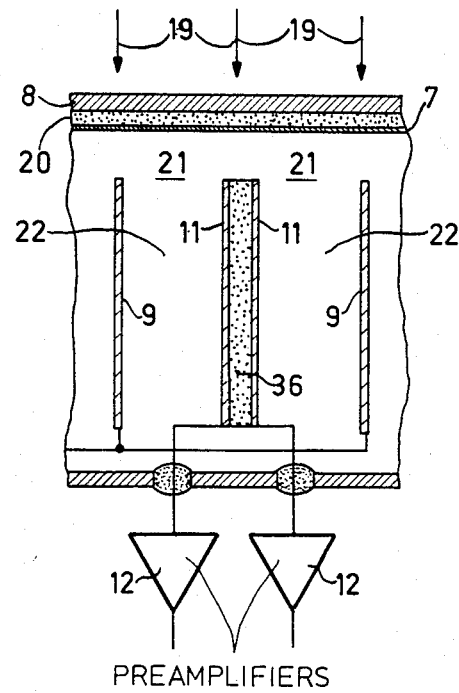
FIGS. 2a-2e, 3, 3a and 5 are partly schematic, partly cross-sectional views of preferred embodiments of a detector according to the invention which can be used for such an X-ray scanner.
Figure 2B:
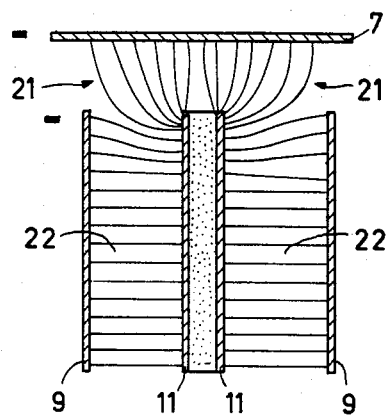
Figure 2C:
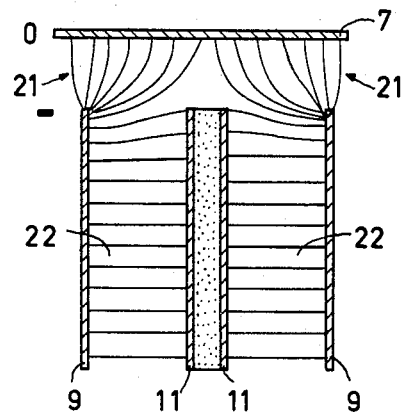

The improved separation of the soft spectrum image information and the hard spectrum image information will be readily understood on the basis of an embodiment of a detector according to the invention as shown in FIGS. 2a, 2b, and 2c. In the soft spectrum mode of the X-ray tube (FIG. 2b), the auxiliary electrode 7 which is mounted directly on the entrance window but insulated therefrom by an insulating layer 20, is at a potential which is at least substantially equal to the potential of the high voltage electrodes, for example a voltage of −0.5 KV with respect to the signal electrodes 11. Electrons generated in a region 21 of the ionization chamber 22 adjacent to the auxiliary electrode are then driven to the signal electrode, thus contributing to the measurement signal. It is the soft radiation which gives rise to ionization notably in the region 21. The softer region of the soft spectrum, therefore, will be favored by this step. The harder radiation of the soft spectrum will cause only comparatively little ionization, so that no intensification will occur.

Conversely, in a hard spectrum mode of the X-ray tube (FIG. 2c) auxiliary electrode is adjusted to a potential which is at least substantially equal to the potential of the signal electrodes. As a result, electrons produced by ionization in the region 21 will be driven to the auxiliary electrode, so that they will not contribute to the measurement signal. The softer radiation of the hard spectrum, will consequently be dissipated in favor of the harder radiation thereof. The signals measured in both modes, consequently, will be more nearly indicative of the desired radiation energy as a result of this step.

Figure 2D:
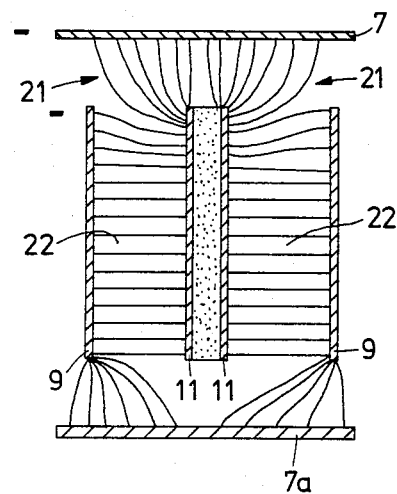
Figure 2E:
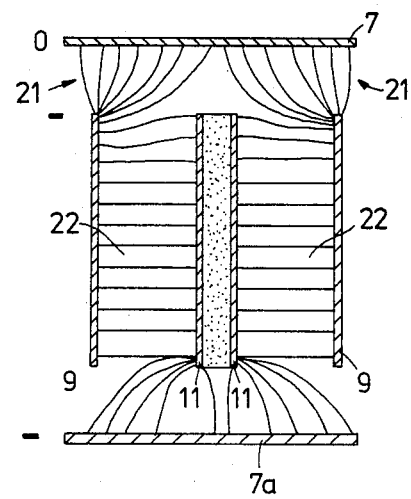

When a corresponding auxiliary electrode 7a is mounted in phase-opposition (opposite potential) with respect to the first auxiliary electrode near the exit face, that is to say opposite the entrance window of the detector, the harder radiation of the soft spectrum will be dissipated in that region (FIG. 2d), or the harder radiation of the hard spectrum will be favored (FIG. 2e), so that the discriminating effect will be intensified.

Figure 3:
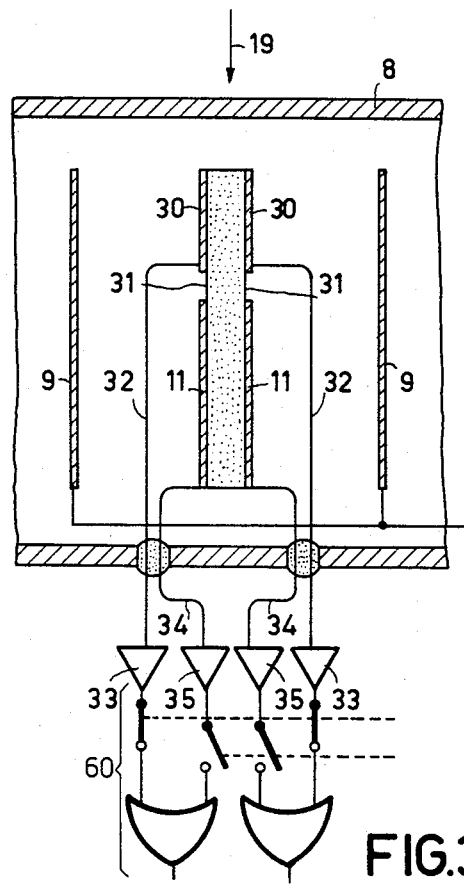

In a detector as shown in FIG. 3, an auxiliary electrode 30 forms a part of the signal electrode. As a result, better discrimination between the hard and soft spectra can be achieved, especially if there is a sufficiently wide gap 31 between the signal electrode and the auxiliary electrode. A wider gap, however, has the drawback that the sensitivity of the detector as such is reduced. The auxiliary electrodes 30 are connected, via leads 32, to preamplifiers 33 and the actual signal electrodes 11 are connected to preamplifiers 35 via leads 34. A switching mechanism 60 can be used to ensure that to detect a soft spectrum the electrodes 30 are read and that to detect a hard spectrum the electrodes 11 are read. It will be clear from the foregoing that soft radiation produces comparatively more ionization near the electrode 30 and that hard radiation produces comparatively less ionization in this region.

Figure 3A:
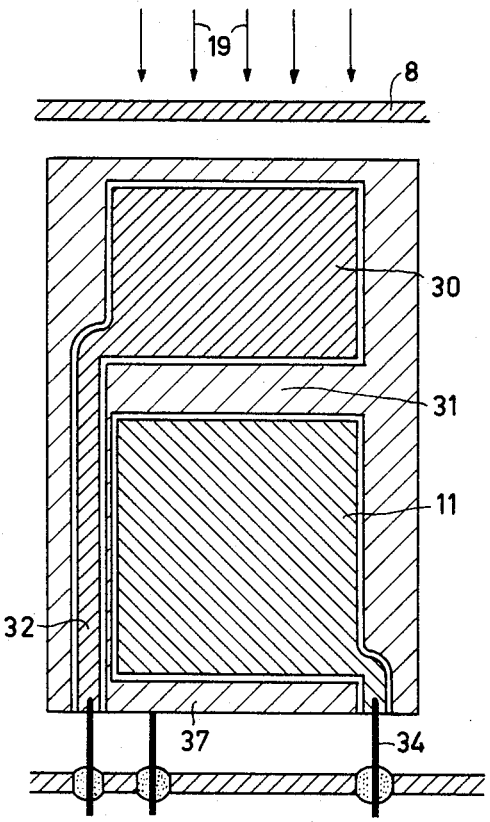

FIG. 3a shows a practical embodiment of a detector comprising a divided signal electrode. The electrodes are arranged on an electrically insulating plate 36 (FIG. 2a). In order to prevent disturbing leakage currents, a guard electrode 37 is provided. In a detector with a mutually asymmetrical cell construction as shown in FIG. 2, corresponding electrodes are arranged on the rear of the insulating plate 36 which may be, for example, a so-called printed circuit board. For a detailed description of a detector including a double signal electrode, reference is made to an article by Aaron Fenster entitled "Split Xenon Detector for Tomochemistry" (*Journal of Computer Assisted Tomography*, Vol. 2. pp. 243–252, July 1978).

Figure 4:
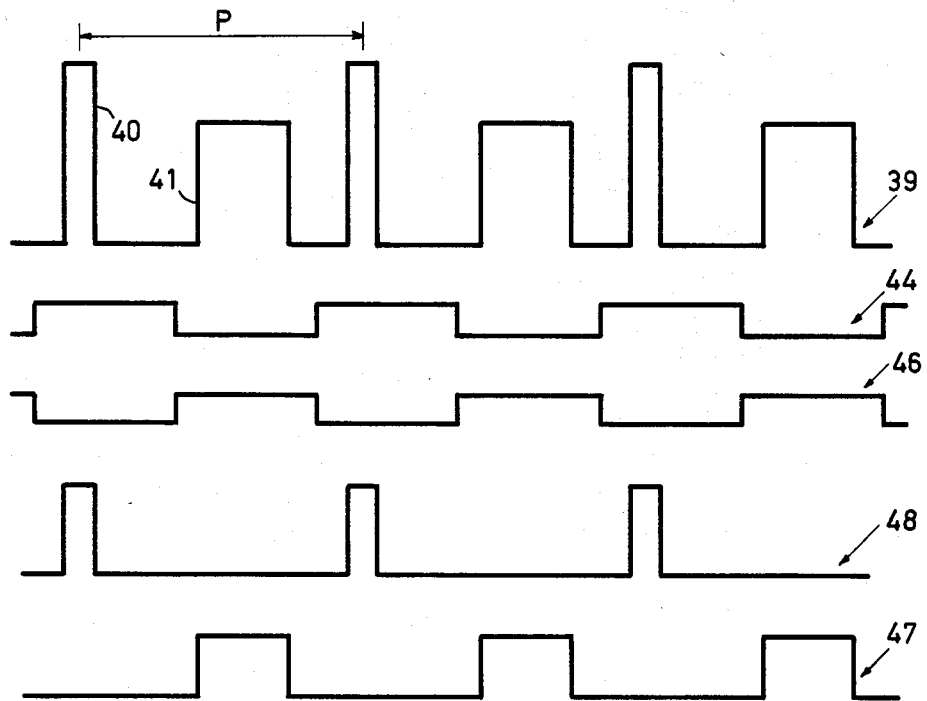
FIG. 4 shows waveform diagrams for the pulsed operation of a radiation source illustrating switching pulses for the electrode potentials and the measurement pulses to be obtained.

FIG. 4 graphically shows how a high voltage generator can be operated for the usual dual energy measurement. Curve 39 represents the voltage applied to the X-ray source. In order to obtain ultimate signals having approximately the same amplitude, a different pulse duration is used for the alternating high voltage pulses 40 and low voltage pulses 41. The repetition frequency of the pulses is, for example, such that during one rotation there are 1200 pulses. From these 1200 pulses, two rotationally scanned images, each with 600 measurement directions, can be reconstructed. During reconstruction, an apparent rotation can be added for one of the images in order to make both images register exactly.

Using switching pulses (not shown) having the relationship indicated by the curves 44 and 46 for the switching mechanism, the pulse pattern 44 being applied to the electrodes 30 and the pulse pattern 46 to the electrodes 11, measurement pulses 47 are obtained for a low energy spectrum and measurement pulses 48 are obtained for a high energy spectrum. The energy content of both pulses is then substantially the same, neglecting of course the differences in absorption. This is an optimum condition for further image processing, and notably for the combination of the two images as performed during image subtraction.

Figure 5:
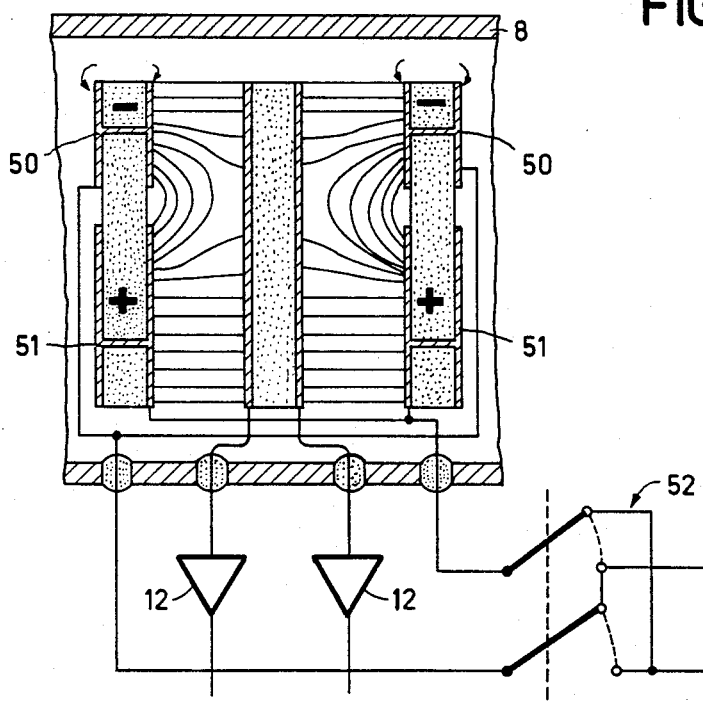

FIG. 5 shows a detector in which the high voltage electrodes are divided into two portions, that is to say a portion 50 for measuring mainly soft radiation and a portion 51 for measuring mainly hard radiation. The signal electrodes, being asymmetrical, are connected to a signal processing device (not shown) via preamplifiers 12. The high voltage electrodes 50 may all be interconnected, providing a major advantage over the embodiment comprising a divided signal electrode. The electrodes 51 may also be interconnected. Electrodes 50 and 51 are connected to a switching mechanism 52.

A discriminating measurement mode can be achieved by switching the potential of the electrodes in phase with the high voltage pulses of the X-ray source between, for example, 0 volts and a high voltage potential by means of the switch 52. During the measurement with a soft spectrum, the electrodes 50 carry a high voltage potential so that the electrons produced in this region are driven onto the signal electrode and contribute to the measurement signal. The electrons produced by the hard radiation, which penetrates as far as the electrodes 51, are not driven onto the signal electrode, because the electrodes 51 carry a potential which is the same as the signal electrode. Hence, these electrons do not contribute to the measurement signal. The reverse process takes place during measurement with a hard radiation spectrum.

According to another method of measurement, the electrodes 50 are adjusted to a highly negative potential and the electrodes 51 to a highly positive potential with respect to the signal electrode. Ionization near the electrodes 50 then produces an electron current onto the signal electrode. Ionization due to harder radiation near the electrode 51 produces an ion current onto the signal electrode which at least partly compensates for the former electron current. The measurement signal is therefore a signal formed by the difference between the electron current and the ion current. Therefore, a difference signal representing the relative amount of ionization produzed by soft radiation and by hard radiation. This measurement can be performed without reversing of the electrode potentials for the soft spectrum mode and for the hard spectrum mode respectively. In order to intensify the discrimination, however, switching may be performed. For this purpose it is necessary to interchange the electrode potentials.

This method of measurement adjusts the detector signal such that the negative part of the detector signal generated by the hard radiation spectrum can be compensated for by the soft spectrum response. The high voltages of the X-ray tube can also be selected so that the region in which the response to the hard radiation spectrum has a zero crossing from negative to positive, corresponds to the energy limit of the response of the soft energy spectrum. For this adjustment a value q can be found for which:

$$q \int_0^{E_c} L\,dE + \int_0^{E_c} H\,dE = O$$

In this equation, L is the soft spectrum response, H is the hard spectrum response, $E_c$ is the energy limit of the response to the soft spectrum, q is the pulse length ratio of the pulses for the soft spectrum to the pulses for the hard spectrum.

The modified measurement signals are then $Hm = H + L$ and $LM = L$ or $HM = L - H$ and $LM = L$. The first modification applies to the situation in which the electrodes 50 carry a positive potential and the electrodes 51 carry a negative potential, and the second modification applies to the situation in which these potentials have been interchanged. This method can result in complete wavelength separation for both modes. For the modification in which $Hm = H + L$ it is possible to read the detector after the soft radiation pulse, resulting in a measurement signal $Lm$, without reset of the integrator of the preamplifier. This is followed by the hard radiation pulse which produces a measurement signal $Hm$. Reset takes place only after that. In order to avoid the processing of negative signals by the signal processing device, a signal inverter can be used.

Even though the invention has been described with reference to ionization detectors, it can in principle also be used with detectors comprising a divided scintillation crystal. An additional difficulty, of course, is then presented by the more difficult treatment of optical radiation. Therefore, the system must be adapted thereto, for example, by inversion of a part of the signal obtained from a given part of the crystal.

Regardless of the type of apparatus used, the fact that fluoroscopic images are derived from different wavelengths of radiation will, in itself, have an important diagnostic value and often also provides a more direct link to the therapy to be used. Moreover, the method according to the invention can be successfully used for obtaining mixed images recorded with different radiation hardnesses. Important in this respect are subtraction images of the biological object itself as well as of an object in which a radiation absorbing substance having a wavelength-sensitive absorption characteristic, has been introduced. The measuring method can notably be used in an arrangement for making so-called scanograms.

What is claimed is:

1. A radiography apparatus comprising:
    a radiation source for generating at least two different energy spectra of radiation;
    a radiation detector for measuring the radiation from the source which is incident thereon, said detector comprising an ionization chamber having first and second ends, the first end being nearer to the radiation source than the second end, said chamber having an entrance window at the first end thereof;
    a high voltage electrode in the ionization chamber extending in a direction from the first end toward the second end of the detector, said high voltage electrode having an electric potential;
    a signal electrode in the ionization chamber extending in a direction from the first end toward the second end of the detector, said signal electrode being separated from the high voltage electrode by a space which is located behind the entrance window, said signal electrode having electric potential;
    an auxiliary electrode in the ionization chamber and arranged substantially parallel to and near the entrance window; and
    a voltage source having an output electrically connected to the auxiliary electrode, the output of said voltage source selectively switchable between two different values so as to selectively favor the measurement of radiation absorbed at locations toward the first end of the detector or to selectively favor the measurement of radiation absorbed at locations toward the second end of the detector.

2. A radiography apparatus as claimed in claim 1, characterized in that the output of the voltage source is selectively switchable between values equal to the potential on the high voltage electrode and the potential on the signal electrode.

3. A radiography apparatus as claimed in claim 2, characterized in that:
    the radiation source is an X-ray tube connected to a voltage supply which is switchable between a first high voltage and a second high voltage which is higher than the first; and when the voltage supplied to the X-ray tube is at the first high voltage, the potential on the auxiliary electrode is equal to the potential on the high voltage electrode; and when the voltage supplied to the X-ray tube is at the second high voltage, the potential on the auxiliary electrode is equal to the potential on the signal electrode.

4. A radiography apparatus as claimed in claim 3, characterized in that the radiation measuring means further comprises:

a second auxiliary electrode in the ionization chamber and arranged substantially parallel to the entrance window at the second end of the detector; and a voltage source having an output electrically connected to the second auxiliary electrode, the output of said voltage source selectively switchable between values equal to the potential on the high voltage electrode and the potential on the signal electrode, the potential on the second auxiliary electrode being equal to the potential on the signal electrode when the potential on the first auxiliary electrode is equal to the potential on the high voltage electrode, and the potential on the second auxiliary electrode being equal to the potential on the high voltage electrode when the potential on the first auxiliary electrode is equal to the potential on the signal electrode.

5. A radiography apparatus comprising:

a radiation source for generating at least two different energy spectra of radiation; and a radiation detector for measuring the radiation from the source which is incident thereon, said radiation detector comprising an ionization chamber having first and second ends, the first end being nearer to the radiation source than the second end, said chamber having an entrance window at the first end thereof;

characterized in that:

the detector further comprises means for measuring the radiation absorbed within the detector, said means selectively favoring the measurement of radiation absorbed at locations toward the first end of the detector or selectively favoring the measurement of radiation absorbed at locations toward the second end of the detector; and the measuring means comprises:

a high voltage electrode in the ionization chamber extending in a direction from the first end toward the second end of the detector, said high voltage electrode having a first portion at a location toward the first end of the detector and having a second portion at a location toward the second end of the detector, said first and second portions being electrically insulated from one another; and a signal electrode in the ionization chamber extending in a direction from the first end toward the second end of the detector, said signal electrode being separated from the high voltage electrode by a space which is located behind the entrance window.

* * * * *